(12) United States Patent
Mostov et al.

(10) Patent No.: US 6,340,743 B1
(45) Date of Patent: Jan. 22, 2002

(54) ANTIBODIES TO PIGR STALK

(75) Inventors: Keith E. Mostov; Janice Richman-Eisenstat, both of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/475,088

(22) Filed: Dec. 30, 1999

Related U.S. Application Data

(62) Division of application No. 08/856,383, filed on May 14, 1997, now Pat. No. 6,042,833.
(60) Provisional application No. 60/018,958, filed on Jun. 4, 1996.

(51) Int. Cl.⁷ .......................... C07K 16/28; C07K 16/46
(52) U.S. Cl. ................... 530/387.9; 530/387.3; 530/387.5; 530/388.22; 530/389.1; 530/391.1; 530/391.3; 530/391.7
(58) Field of Search ............... 530/387.1, 387.3, 530/387.5, 387.9, 388.1, 388.22, 389.1, 391.1, 391.3, 391.7; 424/130.1, 133.1–135.1, 132.1, 139.1, 141.1, 143.1, 178.1, 182.1, 183.1

(56) References Cited

PUBLICATIONS

Breitfeld et al., *J. Cell Biology* 109:475–486 (1989).
Piskurich et al., *Journal of Immunology* 154:1735–1747 (1995).
Ferkol et al., *J. Clin. Invest.* 95:493–502 (1995).
Wu et al., *J. Biol. Chem.* 262:4429–4432 (1987).
Breitfeld et al., *Methods in Cell Biology* 32:329–337 (1989).
Eiffert et al., *Physiol. Chem.* 365:1489–1495 (1984).
Solari et al., *J. Histochemistry and Cytochemistry* 34(1):17–23 (1986).
Ferkol et al., *J. Clin. Invest.* 92:2394–2400 (Nov. 1993).
Mostov et al., *Ann. Rev. Immunol.* 12:63–84 (1994).
Mazanec et al., *J. Virol.* 69(2):1339–1343 (Feb. 1995).
Williams, G., *TIBTECH* 6:36–42 (Feb. 1988).
Hudson, L., et al. (ed), Practical Immunology, 2nd edition, pp. 192–202 (1980).
Solari, R., et al., J. Biol. Chem. 260:1141–1145, Antibodies recognizing different domains of the polymeric immunoglobulin receptor. (1985).
Mostov, Keith E., et al., *Nature*, 308(5954):37–43 (Mar. 1, 1984).
Mostov, Keith E., et al., *Proc. Natl. Acad. Sci.*, USA 77(12):7257–7261 (Dec. 1980).

*Primary Examiner*—Phillip Gambel
*Assistant Examiner*—Jessica H. Roark
(74) *Attorney, Agent, or Firm*—Townsend and Townsend and Crew LLP

(57) ABSTRACT

Antibody ligands are provided for specific binding to the stalk of a polymeric immunoglobulin receptor (plgr) of a cell with the proviso that the ligand does not substantially bind to secretory component of plgR under physiological conditions. The ligand may be targeted to, into, or across the cell and may comprise a biologically active composition.

9 Claims, No Drawings

ANTIBODIES TO PIGR STALK

This application is a divisional of application Ser. No. 08/856,383, filed May 14, 1997, and issued as U.S. Pat. No. 6,042,833 on Mar. 28, 2000, and claims the benefit of U.S. Provisional Application No. 60/018,958, filed Jun. 4, 1996, the disclosure of which is incorporated by reference.

FIELD OF THE INVENTION

The present invention relates, in general, to compositions and methods for the specific binding of a ligand to the stalk region of the polymeric immunoglobulin receptor for internalization into, or transport across, a cell.

BACKGROUND OF THE INVENTION

One of the most challenging problems facing the pharmaceutical and biopharmaceutical industries is delivering therapeutic agents past the various semi-permeable membranes within the body. Particularly in the case of macromolecules, the obstacle to cost effective or convenient treatment is often due to the lack of an adequate drug delivery system. In turn, this issue dictates whether production of a drug is economically feasible. Thus the search for alternative delivery systems often rivals the search for new drugs themselves.

Gene transfer methods can be viewed as a paradigm of macromolecular drug delivery. These methods can be divided into three categories: physical (e.g., electroporation, direct gene transfer, and particle bombardment), chemical (e.g., proteinoids, microemulsions, and liposomes), and biological (e.g., virus-derived vectors, and receptor-mediated uptake). Amongst biological transfer methods, receptor-mediated uptake is a particularly promising approach. Targeting a ligand to an endocytosed receptor acts as a means to ferry that ligand into the cell. However, one drawback of receptor-mediated systems has been their general reliance on intravenous administration which severely limits their use.

Mucosal epithelial cells line a number of readily accessible tissues such as those found in the upper respiratory and gastrointestinal tracts. The accessibility of these cells make them an attractive target for drug delivery. See, e.g., Ferkol et al., J. Clin. Invest. 92:2394–2400 (1993); Ferkol et al., J. Clin. Invest. 95:493–502 (1995). Retrograde transport of an antibody from the lumenal to the basolateral surface of epithelial cells has been reported, albeit at very low levels. Breitfeld et al., J. Cell Biology 109:475–486 (1989). In that study, movement across the cell was followed by binding an antibody to the secretory component of polymeric immunoglobulin receptor (pIgR). Relative to the level of basolateral to apical transport, Breitfeld et al. reported that less than 5% of the transport was retrograde in nature. The nominal level of counter-transport minimizes the utility of secretory component as a means to deliver biologically active compositions into cells. Moreover, due to the abundance of cleaved pigR in the lumen, binding of ligand to cleaved pIgR, rather than the intact pigR of the cell surface, would diminish the utility of pIgR counter-transport as a mechanism of drug delivery.

Accordingly, what is needed in the art is a means to convey ligands into or across a cell surface with high efficiency. More particularly, what is needed in the art is a means to deliver macromolecules to, into, or across cells lining the gastrointestinal or respiratory tracts. The present invention provides these and other advantages.

SUMMARY OF THE INVENTION

In one aspect, the present invention is directed to a ligand that binds specifically to the stalk of a polymeric immunoglobulin receptor (pIgR) of a cell with the proviso that the ligand does not substantially bind to secretory component of pIgR under physiological conditions. Typically, the antibody specifically binds only to the stalk. In one embodiment, the ligand is an antibody, preferably a humanized antibody. In another embodiment the ligand is a recombinant single chain variable region fragment of an antibody. In yet another embodiment the ligand binds to an extracellular epitope within the first 33 amino acids that are cell membrane proximal to a cleavage site of the receptor.

The ligand may comprise a binding component for binding to the stalk, and a biologically active component such as a nucleic acid, protein, radioisotope, lipid, and carbohydrate. Biologically active components comprise anti-inflammatories, anti-infectives, anti-sense oligonucleotides, antibiotics, and anti-infectives. In one embodiment, the biologically active component is a nucleic acid encoding a wildtype cystic fibrosis transmembrane conductance regulator. In a preferred embodiment the cell is an epithelial cell, most preferably a mammalian epithelial cell.

In another aspect, the present invention is directed to a method of introducing a ligand into a cell expressing a polymeric immunoglobulin receptor by attaching the ligand to the stalk of the polymeric immunoglobulin receptor of the cell with the proviso that the ligand does not substantially bind to the secretory component of pIgR under physiological conditions. In one embodiment, the ligand is attached to the stalk at the apical surface of a cell; and in further embodiments, the ligand is transcytosed to the basolateral surface of the cell, and released from the stalk at the basolateral surface.

In a further aspect, the present invention relates to a method of attaching a ligand to a cell expressing a polymeric immunoglobulin receptor comprising the step of binding the ligand to a stalk of the receptor with the proviso that the ligand does not substantially bind to secretory component of pIgR under physiological conditions. In one embodiment, the ligand is introduced into the cell after binding. Alternative embodiments of the present invention may be had by reference to the various aspects of the present invention.

Amongst the various in vivo and in vitro utilities, the present invention may be used to transport therapeutic or diagnostic compositions to, into, or across, mucosal epithelial cells. Thus, the invention provides a highly efficient and convenient means to transfer nucleic acids or proteins into epithelial cells.

DESCRIPTION OF THE PREFERRED EMBODIMENT

The present invention is directed to a ligand that binds specifically to the stalk of a polymeric immunoglobulin receptor (pIgR) of a cell with the proviso that the ligand does not substantially bind to secretory component of pIgR under physiological conditions. The invention provides, inter alia, methods of attaching and introducing a ligand into a cell expressing pIgR.

After transport to the apical surface of epithelial cells, the majority of pIgR is cleaved and secretory component is released. We have discovered that, surprisingly and unexpectedly, cleavage of intact pIgR in the lumen leaves a residual extracellular region of pIgR (i.e., the "stalk") intact; and further, the stalk remains accessible to binding despite the abundance of proteases typically present in lumenal milieu. The ability to bind, endocytose, and transcytose a ligand bound to the pIgR stalk provides, in part, the invention as disclosed and claimed herein.

The present invention has utility as a means of transporting therapeutic or diagnostic compositions to, into (endocytosis) or across (transcytosis) a cell expressing pIgR. Thus the invention can be used to transport biologically active compositions such as proteins, nucleic acids, or detectable labels specifically to cells expressing pIgR. The invention also provides a means of labeling and distinguishing epithelial cells from amongst a mixed cell population in pathological studies. Further, since pIgR expression is reduced in carcinomas relative to normal epithelium, the labeling of pIgR has utility as a diagnostic adjunct in endoscopic or radiologic procedures. Additionally, binding of therapeutic ligands to plgr has utility in extending their duration in the lumen of various passageways and increasing their effectiveness.

Definitions

Unless defined otherwise herein, all technical and scientific terms used herein have the same meaning as commonly understood by one of ordinary skill in the art to which this invention belongs. Singleton et al. (1994) *Dictionary of Microbiology and Molecular Biology*, second edition, John Wiley and Sons (New York), and Hale and Marham (1991) *The Harper Collins Dictionary of Biology*, Harper Perennial, N.Y. provide one of skill with a general dictionary of many of the terms used in this invention. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. For purposes of the present invention, the following terms are defined below.

By "ligand" or "ligand binding moiety", is meant all molecules capable of specifically binding to the polymeric immunoglobulin receptor (pIgR). Ligands include, but are not limited to, antibodies, proteins, peptides, nucleic acids, lipids, and carbohydrates.

By "biologically active component" is meant a compound which, in vivo, directly causes or inhibits an increase or decrease in cellular transcription, translation, receptor binding, active or passive transport, cell signaling, signal transduction, cell division, cell differentiation, cell death, cell adhesion, cell movement, cell morphology, metabolism, enzyme activity, apoptosis, protein degradation, protein movement (e.g., secretion), protein stability, or phosphorylation. Biologically active components also comprise diagnostic compositions which allow the foregoing events to be assessed.

By "bind(s) specifically" or "specifically bind(s)" or "attached" or "attaching" is meant the preferential association of a ligand, in whole or part, with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific binding, may be distinguished as mediated through specific recognition of the target molecule. Typically specific binding results in a much stronger association between the delivered molecule and cells bearing the target molecule than between the bound molecule and cells lacking the target molecule. Specific binding typically results in greater than 2 fold, preferably greater than 5 fold, more preferably greater than 10 fold and most preferably greater than 100 fold increase in amount of bound ligand (per unit time) to a cell or tissue bearing the target molecule as compared to a cell or tissue lacking the target molecule or marker.

By "stalk" is meant the extracellular component of the polymeric immunoglobulin receptor (pIgR) that corresponds to that region of pIgR that is bound to the cell following cleavage of that segment of pIgR which constitutes the secretory component. The stalk is present regardless of whether the segment of pIgR which corresponds to secretory component is cleaved or uncleaved from pIgR.

By "pIgR" or "polymeric immunoglobulin receptor" is meant the receptor which is expressed in mucosal epithelial cells, including airway epithelial cells, submucosal gland cells, intestinal cells, nasal epithelium, breast, oral mucosa, urinary and reproductive tract epithelium, and conjunctival tissue, and is implicated in basolateral to apical transcytosis of dimeric immunoglobulin A (digA) and/or pentameric IgM.

By "not substantially bind" is meant that no more than 15% of a ligand which specifically binds to a target molecule is bound to a particular non-target molecule. More preferably, no more than 10% is bound to the non-target molecule, even more preferably less than 5%, and most preferably less than 1%.

By "secretory component" is meant that extracellular portion of pIgR which is generally cleaved following basolateral to apical transcytosis. Typically, the secretory component comprises the dimeric IgA (dIgA) binding portion of pIgR. Secretory component is typically released into the lumen with or without dIgA bound to the secretory component.

By "physiological conditions" is meant an extracellular milieu having conditions (e.g., temperature, pH, and osmolarity) which allows for the sustenance or growth of a cell of interest.

By "antibody" is meant an immunoglobulin molecule obtained by in vitro or in vivo generation of the humoral response, and includes both polyclonal and monoclonal antibodies. The term also includes genetically engineered forms such as chimeric antibodies (e.g., humanized murine antibodies), heteroconjugate antibodies (e.g., bispecific antibodies), and recombinant single chain Fv fragments (scFv). The term "antibody" also includes antigen binding forms of antibodies (e.g., Fab, F(ab)$_2$).

By "humanized antibody" is meant an antibody which comprises a non-human amino acid sequence but whose constant region has been altered to reduce immunogenicity in humans.

By "wildtype cystic fibrosis transmembrane conductance regulator" is meant a functional form of the cystic fibrosis transmembrane conductance regulator (CFTR). Riordan et al., Science, 245:1066–1073 (1989).

By "apical surface" is meant that surface of a cell to which intact pIgR is transcytosed to after endocytosis from the basolateral surface. Generally, the apical surface of the cell adjoins a lumen and therein intact pIgR is cleaved to release the secretory component.

By "basolateral surface" is meant that surface of a cell from which intact pIgR is delivered to after synthesis in the endoplasmic reticulum and passage through the Golgi complex.

By "surface of the stalk" is meant the extracellular region of the stalk.

By "released" is meant the interference in the specific association of a ligand, in whole or part, with its target molecule.

By "transcytosed" or "transcytosis" is meant conveyance from one plasma membrane of the cell to another via an intracellular route. Typically, transcytosis occurs from the basolateral to apical or apical to basolateral plasma membrane of the cell.

By "cell membrane proximal" is meant next to or nearer the cell membrane.

By "extracellular" is meant the region extending outward from the lipid bilayer encompassing a cell.

Identification of pIgR

The nucleic acid and amino acid sequence of the polymeric immunoglobulin receptor has been identified in a variety of taxonomically diverse species. See, Piskurich et al., *Journal of Immunology* 154:1 735–1747 (1995). Identification of pIgR from other species can be accomplished by any number of methods well known to those of skill in the art. For example, using published pIgR sequences a nucleic acid probe to plgR can be constructed. The probe typically should be derived from a conserved region of plgR. Hybridization of the probe to a genomic or cDNA library can be used to identify pIgR in an unknown species. It will be understood by the skilled artisan that the nucleic acid sequence of the pIgR probe should generally be that of the species most closely related to the probed species. An extensive guide to the hybridization of nucleic acids is found in Tijssen (1993) *Laboratory Techniques in Biochemistry and Molecular Biology—Hybridization with Nucleic Acid Probes* Part I, Chapter 2 "Overview of principles of hybridization and the strategy of nucleic acid probe assays", Elsevier, N.Y.

In an alternative approach, pIgR or peptide fragments thereof (e.g., secretory component) can be used to create antibodies to screen expression libraries. See, e.g., Ferkol et al., *J. Clin. Invest*. 95:493–502 (1995). These and other methods well known to the skilled artisan may be found, for example, in Berger and Kimmel, *Guide to Molecular Cloning Techniques, Methods in Enzymology* volume 152 Academic Press, lnc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Confirmation of the identity of a nucleic acid or protein as encoding pIgR may be had by such approaches as constructing antibodies to the putative pIgR protein and confirming the ability of these antibodies to bind to a protein having the characteristics of pIgR (e.g., being present on the surface of epithelial cells, binding of dimeric IgA or pentameric IgM, etc.).

Identification of the Stalk

The stalk can be identified by a variety of techniques well known to those of skill. A putative heptapeptide consensus sequence which identifies the cleavage site of pIgR and thereby defines the amino terminus of the stalk has been identified. The sequence Phe-Ala-Xaa-Glu (SEQ ID NO:1), where Xaa is a polar or charged amino acid, was identified as immediately preceding this putative cleavage site. Piskurich et al., *Journal of Immunology* 154:1735–1747 (1995). Cleavage at the consensus site liberates the secretory component and defines its carboxy terminus. The carboxy terminus of secretory component may be altered by secondary cleavage events (e.g., exopeptidase or endopeptidase activity) to yield secondary carboxy termini. Id. However, the amide linkage which initially defines the amino terminus of the stalk and the carboxy terminus of secretory component may be identified by sequence alignment and identification of the cleavage consensus sequence.

Methods of alignment of sequences for comparison are well-known in the art. Optimal alignment of sequences for comparison may be conducted by the local homology algorithm of Smith and Waterman (1981) *Adv. Appl. Math.* 2: 482; by the homology alignment algorithm of Needleman and Wunsch (1970) *J. Mol. Biol*. 48: 443; by the search for similarity method of Pearson and Lipman (1988) *Proc. Natl.*

*Acad. Sci. USA* 85: 2444; by computerized implementations of these algorithms (including, but not limited to CLUSTAL in the PC/Gene program by Intelligenetics, Mountain View, Calif., GAP, BESTFIT, FASTA, and TFASTA in the Wisconsin Genetics Software Package, Genetics Computer Group (GCG), 575 Science Dr., Madison, Wis., USA); the CLUSTAL program is well described by Higgins and Sharp (1988) Gene, 73: 237–244 and Higgins and Sharp (1989) *CABIOS* 5: 151–153; Corpet, et al. (1988) *Nucleic Acids Research* 16, 10881–90; Huang, et al. 1992) *Computer Applications in the Biosciences* 8, 155–65, and Pearson, et aL (1994) *Methods in Molecular Biology* 24, 307–31. Alignment is also often performed by inspection and manual alignment.

In another approach, secretory component can isolated from fluids in the apical lumen (e.g., milk or bile) and sequenced by amino acid sequencing methods well known to those of skill such as Edman degradation, or mass spectrometry. Eiffert et al., *Hoppe-Seyler's Z. Physiol. Chem*. 365:1489–1495 (1984). Amongst the various secondary carboxyl ends defined by secondary cleavage events, the carboxy terminal amino acid adjacent to the cleavage site can be identified.

Peptides which correspond to the pIgR stalk of selected species include:

Mouse: Glu-Arg-Glu-Ile-Gln-Asn-Ala-Gly-Asp-Gln-Ala-Gln-Glu-Asn-Arg-Ala-Ser-Gly-Asn-Ala-Gly-Ser-Ala Gly-Gly-Gln-Ser-Gly-Ser-Ser-Lys(SEQ ID NO:2)

Rat: Glu-Arg-Glu-lIe-Gln-Asn-Ala-Gly-Asp-Gln-Ala-Gln-Glu-Asn-Arg-Ala-Ser-Gly-Asn-Ala-Gly-Ser-Ala-Gly-Gly-Gln-Ser-Gly-Ser-Ser-Lys(SEQ ID NO:3)

Human: Glu-Lys-Ala-Val-Ala-Asp-Thr-Arg-Asp-Gln-Ala-Asp-Gly-Ser-Arg-Ala-Ser-Val-Asp-Ser-Gly-Ser-Ser-Glu-Glu-GIn-Gly-Gly-Ser-Ser-Arg (SEQ ID NO:4)

Bovine: Glu-Ser-Val-Lys-Asp-Ala-Ala-Gly-Gly-Pro-Gly-Ala-Pro-Ala-Asp-Pro-Gly-Arg-Pro-Thr-Gly-Tyr-Ser-Gly-Ser-Ser-Lys(SEQ ID NO:5)

Rabbit: Leu-Ala-Glu-Val-Ala-Val-GIn-Ser-Ala-Glu-Asp-Pro-Ala-Ser-Gly-Asp-Pro-Ala-Ser-Gly-Ser Arg-Ala-Ser-Val-Asp-Ser-Gly-Ser-Ser-Glu-Glu-Gln Gly-Gly-Ser-Ser-Arg-Ser-Lys (SEQ ID NO:6)

Cells Expressing pIgR

While the present invention broadly pertains to eukaryotic cells. The pIgR expressing cell of the present invention is preferably a mammalian cell and more preferably a mammalian epithelial cell that normally secretes IgA. Mammalian cells can be transfected with a nucleic acid encoding pIgR isolated, synthesized or otherwise derived from one or more desired species. Methods of transfecting and expressing genes in mammalian cells are known in the art. Transducing cells with viral vectors can involve, for example, incubating viruses with cells within the viral host range under conditions and concentrations necessary to cause infection. See, e.g., *Methods in Enzymology*, vol. 185, Academic Press, Inc., San Diego, Calif.(D.V. Goeddel, ed.) (1990) or M. Krieger, *Gene Transfer and Expression—A Laboratory Manual*, Stockton Press, New York, N.Y., (1990) and the references cited therein.

The culture of cells which can be used in the present invention include cell lines and cultured cells from tissue or blood samples is well known in the art. Freshney (*Culture of Animal Cells, a Manual of Basic Technique, third edition* Wiley-Liss, N.Y. (1994)) and the references cited therein provides a general guide to the culture of cells. The nucleic acid sequences encoding pIgR from the desired species may be expressed in a variety of eukaryotic host cells, including yeast, and various higher eukaryotic cells such as the COS, CHO and HeLa cells lines and myeloma cell lines as well as MDCK and human colon carcinoma derived cells such as Caco2. The recombinant protein gene will be operably linked to appropriate expression control sequences for each host. For eukaryotic cells, the control sequences will include a promoter and preferably an enhancer derived, for example, from immunoglobulin genes, SV40, cytomegalovirus, etc., and a polyadenylation sequence, and may include splice donor and acceptor sequences.

Binding Ligands to the Stalk

The specific stalk binding ligand is not critical to this invention and various ligands may be used. A host of methods for construction and selection of ligands such as nucleic acids, proteins or peptides (collectively, "peptides), or antibodies, or small organics or inorganics (e.g., U.S. Pat. No. 5,143,854; WO 90/15070; WO 92/10092; WO 96/11878) having the desired specific binding characteristics are well known in the art. Preferably, ligands of the present invention will, under physiological conditions, bind to the stalk without substantially binding to the secretory component of pIgR. More preferably, the ligands of the present invention specifically bind only to the stalk under physiological conditions. Typical physiological conditions vary from tissue to tissue. However, exemplary physiological conditions are encountered in the gastrointestinal or respiratory tract of mammals, including but not limited to humans. A ligand may be chosen to bind to an extracellular ligand binding site ("epitope") contained within the first 6, 9, 12, 15, 18, 21, 24, 27, 30, or 33 membrane proximal amino acids of the stalk.

Antibodies, including polyclonal, monoclonal, or recombinant single chain Fv antibodies, can be constructed for use as ligands in the present invention. Methods of producing polyclonal and monoclonal antibodies are known to those of skill in the art. See, e.g., Coligan (1991) *Current Protocols in Immunology* Wiley/Greene, N.Y.; and Harlow and Lane (1989) *Antibodies: A Laboratory Manual* Cold Spring Harbor Press, N.Y.; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495–497; See, Huse et al. (1989) *Science* 246: 1275–1281; and Ward, et al. (1989) *Nature* 341: 544–546. Birch and Lennox, *Monoclonal Antibodies: Principles and Applications*, Wiley-Liss, N.Y., N.Y. (1995).

Other suitable techniques for antibody or peptide ligand preparation include selection of libraries of recombinant antibodies/peptides in phage or similar vectors. High affinity antibodies and peptides to the stalk can be rapidly isolated by using phage display methods to express recombinant single chain Fv (scFv) fragments or peptide ligands on the phage surface. Briefly, genes encoding the surface protein of a phage are altered so as to allow the insertion of an antibody or peptide gene which is expressed as a fusion protein on the surface of the phage that carries the gene. The phage expressing the desired antibody or peptide ligand can be selectively enriched and isolated by virtue of its affinity/avidity for the stalk. The DNA encoding the ligand is packaged in the same phage and which allows the gene encoding the ligand to be isolated. A variety of such methods are amply discussed in the literature and well known to the skilled artisan. See, e.g., Winter et aL, *Annu. Rev. Immunol.* 12:433–455 (1994); Marks et al., *J. MoL Biol.* 222:581–597 (1991); Vaughan et al., *Nature Biotechnology* 14:309–314 (1996), U.S. Pat. Nos. 4,642,334; 4,816,397; 4,816,567; 4,704,692; WO 86/01533; WO 88/09344; WO 89/00999; WO 90/02809; WO 90/04036; EP 0 324 162; EP 0 239 400.

In chemical peptide synthesis, a procedure termed "Divide, Couple and Recombine" (DCR) has been used to produce combinatorial peptide libraries. See, Furka et al, *Int. J. Pept. Protein Res.* 37:487–493 (1991) and Houghten et al., *Nature* 354:84–86 (1991). As an alternative to DCR, peptide mixtures have also been made by direct coupling of monomer mixtures. See, Rutter et al., U.S. Pat. No. 5,010,175. The use of such methods to produce mixtures of other linear polymers, such as "peptoids", has been suggested. See, Simon, et al, *Proc. Natl. Acad. Sci. USA* 89:9367–9371 (1992). In oligonucleotide synthesis, "degenerate" or "wobble" mixtures of oligonucleotide products can be made by, for example, delivery of equimolar mixtures of monomers to an oligonucleotide polymer at specific steps during synthesis. See, Atkinson and Smith, in "Oligonucleotide Synthesis. A Practical Approach", 1984, IRL Press, Oxford, edited by M. Gait, pp 35–81. These methods of synthesizing peptides or oligonucleotides provide large numbers of compounds for testing which, if active, can be readily identified.

Preferably, ligands will be constructed to minimize immunogenicity in the host as, for example, by maximizing the number of autologous (self) sequences present in the ligand. Accordingly, chimeric antibodies having non-xenogenic variable regions are preferred. Particularly preferred are the use of antibodies in which xenogenic portions are excluded, or are essentially limited to the complementarity determining regions as in humanized antibodies.

Ligand Binding and Testing

Binding (i.e., attachment) of the ligand to the stalk of pIgR may occur prior or subsequent to cleavage of secretory component; and the ligand may be attached at the basolateral or apical surface. Thus, the ligand can be endocytosed basolaterally or apically, or be subject to apical to basolateral, or basolateral to apical transcytosis. The fate of the ligand, or any element thereof, will vary according to its physico-chemical characteristics. Accordingly, the properties of the ligand may be selected or designed to perform the desired function at the cell surface, within the endosome, or following transcytosis. For example, varying the sensitivity of a ligand to proteolytic or reducing environments can be used to determine the distribution of ligand bound, internalized, or transported across the cell. Where desirable, a ligand may be designed to remain specifically bound to the cell following attachment or transcytosis or, alternatively, to be released into the extracellular milieu. Thus, the properties of any of the various elements of the ligand, including the binding component, biologically active component or linker, may be designed or selected to allow for different degrees of affinity, stability, or activity at different intracellular compartments or surfaces of the cell, as desired.

A. Ex Vivo Testing of Ligand Binding

In vitro binding of the ligand to the stalk may be conveniently assessed by measuring endocytosis or transcytosis of bound ligand in mammalian epithelial cells. "Endocytosis" refers generally to the phenomenon of a cell ingesting material, e.g., by phagocytosis or pinocytosis. Receptor-mediated endocytosis provides an efficient means of causing a cell to ingest material which binds to a cell surface receptor. See, Wu and Wu (1987) *J. Biol. Chem.* 262:4429–4432; Wagner et al. (1990) *Proc. Natl. Acad. Sci. USA* 87:3410–3414, and EP-A1 0388 758. Any number of well known methods for assaying endocytosis may be sued to assess binding. For example, binding, transcytosis, and internalization assays are described at length in Breiftfeld et al. *J. Cell Biol.* 109:475–486 (1989).

Apical endocytosis is conveniently measured by binding a ligand such as a Fab fragment to the stalk at the apical surface of Madin-Darby canine kidney (MDCK) cells at 4° C., warming to 37° C. for brief periods (0–10 min), and cooling the cells back down to 4° C. Methods of pIgR expression in MDCK cells is well known in the art. Breitfeld et al., *Methods in Cell Biology* 32:329–337 (1989). Fab remaining on the surface are removed by stripping at pH 2.3. Intracellular Fab are those that remain cell-associated after the stripping, while surface-bound Fab are those removed by the acid wash. Controls for non-specific sticking include using pre-immune Fab and/or MDCK cells that are not transfected with pIgR.

Transcytosis can be readily assessed by allowing MDCK cells to bind the Fab at the apical surface at 4° C., warming up to 37° C. for 0–240 min, and then measuring the amount of Fab delivered into the basolateral medium. This basolaterally-delivered Fab is compared to the sum of Fab that remains associated with the cells (intracellular or acid-stripped) and the Fab released back into the apical medium. Alternatively, transcytosis can be assessed by continuously exposing cells to the Fab in the apical medium and measuring accumulation of Fab in the basolateral medium. This method avoids cooling the cells, but does not provide the kinetics of transporting a single cohort of ligand. In both methods degradation of the Fab can be assessed by running aliquots of the transcytosed Fab on SDS-PAGE and probing a Western with anti-chicken antibodies. Non-specific transport (e.g. due to fluid phase endocytosis and transcytosis, or paracellular leakage between cells) can be controlled for by using MDCK cells that are not transfected with the pIgR and/or pre-immune Fab.

B. In Vivo Testing of Ligand Binding

Transcytosis in vivo may conveniently be assessed using pathogen-free experimental animals such as Sprague-Dawley rats. Labelled ligand (e.g., radioiodinated antibody) can be administered into the nares. As will be understood by those of skill in the art, a "label" is a composition detectable by spectroscopic, photochemical, biochemical, immunochemical, electromagnetic, radiochemical, or chemical means such as fluorescence, chemifluoresence, or chemiluminescence. Apical to basolateral transcytosis can be readily determined by measuring delivery of the ligand into the circulation as determined by the presence of label. The integrity of the ligand recovered from the circulation can be assessed by analyzing the ligand on SDS polyacrylamide gel electrophoresis.

Biologically Active Component

The biologically active component of the ligand may be covalently or non-covalently bound to the ligand. For example, chelators may be used to bind various isotopes, or nucleic acids may be bound to the ligand via hydrogen bonds. Biologically active components may also be encompassed within emulsions, proteinoids, or liposomes. As those skilled in the art will understand, such structures may be linked covalently to the ligand via derivatized polar head groups or via membrane integral proteins. Binding components of the ligand may also comprise the biologically active component.

Biologically active components comprise any number of compounds known to those of skill as anti-inflammatories, cytokines, anti-infectives, enzyme activators or inhibitors, allosteric modifiers, or antibiotics. Thus, biologically active component includes such compounds as nucleic acids, proteins, peptides, amino acids or derivatives, glycoproteins, radioisotopes, lipids, carbohydrates, or recombinant viruses. The term "nucleic acid" refers to a deoxyribonucleotide or ribonucleotide polymer in either single- or double-stranded form, and unless otherwise limited, encompasses known analogues of natural nucleotides. Nucleic acids include anti-sense nucleic acids, derivatized oligonucleotides for covalent cross-linking with single or duplex DNA, triplex forming oligonucleotides, or nucleic acids encoding proteins or peptides. Nucleic acids also includes compositions for gene therapy such as those encoding for the wildtype cystic fibrosis transmembrane conductance regulator.

Attaching Biologically Active Compositions to the Ligand

The procedure for attaching a biologically active component to a ligand will vary according to the chemical structure of the component. Generally, the ligands will contain a variety of functional groups which are available for reaction with a suitable functional group on a biologically active molecule to bind the agent thereto. Alternatively, the ligand and/or biologically active component may be derivatized to expose or attach additional reactive functional groups. The derivatization may involve attachment of any of a number of linker molecules such as those available from Pierce Chemical Company, Rockford Ill. A "linker" as used herein refers to a molecule used to join, covalently or non-covalently, the ligand and biologically active component. Suitable linkers are well known to those of skill in the art and include, but are not limited to, straight or branched-chain carbon linkers, heterocyclic carbon linkers, or peptide linkers. See, e.g., Birch and Lennox, *Monoclonal Antibodies: Principles and Applications*, Chapter 4, Wiley-Liss, New York, N.Y.(1995); U.S. Pat. Nos. 5,218,112, 5,090,914; Hermanson, *Bioconjugate Techniques*, Academic Press, San Diego, Calif. (1996).

Where both molecules are polypeptides, the linkers may be joined to the constituent amino acids through their side groups (e.g., through a disulfide linkage to cysteine). A bifunctional linker having one functional group reactive with a group on a particular biologically active component, and another group reactive with a ligand, may be used to form the desired conjugate. Alternatively, derivatization may involve chemical treatment of the component; e.g., glycol cleavage of the sugar moiety of the glycoprotein antibody with periodate to generate free aldehyde groups. The free aldehyde groups on the antibody may be reacted with free amine or hydrazine groups on an agent to bind the agent thereto. (See U.S. Pat. No. 4,671,958). Procedures for generation of free sulfhydryl groups on antibodies or antibody fragments are also known (See U.S. Pat. No. 4,659,839). Many procedure and linker molecules for attachment of various compounds including radionuclide metal chelates, toxins and drugs to proteins such as antibodies are known. See, for example, European Patent Application No. 188,256; U.S. Pat. Nos.,4,671,958, 4,659,839, 4,414,148, 4,699,784; 4,680,338; 4,569,789; and 4,589,071; and Borlinghaus et al. Cancer Res. 47: 4071–4075 (1987)).

It is sometimes desirable to release the conjugated molecule when it has reached a target site. Therefore, conjugates comprising linkages which are cleavable in the vicinity of the target site may be used. Cleaving of the linkage to release the biologically active component from the antibody may be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used. Use of the cis-aconitic acid spacer is useful for releasing biologically active components in endosomes. Similarly, disulfide linkages are cleavable in the reductive environment of the endosomes.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 5,141,648 discloses immunoconjugates comprising linkers of specified chemical structure, wherein the linkage is cleaved in vivo thereby releasing the attached compound (radiotherapeutic agent, drug, toxin, etc.). The linker is susceptible to cleavage at a mildly acidic pH, and is believed to be cleaved during transport into the cytoplasm of a target cell, thereby releasing the biologically active compound inside a target cell. U.S. Pat. No. 4,671,958 includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other components to ligands one skilled in the art will be able to determine a suitable method for attaching a given component to a ligand of the present invention.

Egress of the Ligand from the Endosome

A number of methods well known to the skilled artisan may be used to transport ligand, or any portion thereof, out of the endosome.

A poly-L-lysine/nucleic acid complex bound to a ligand which binds specifically to the stalk can be used for efficient transfection. Ferkol et al., *J. Clin. Invest.*, 92:2394–2400 (1993); and Ferkol et al., *J. Clin. Invest.*, 95:493–502 (1995).

In another approach, poly-L-lysine can be linked, such as by genetic fusion or chemical linkers, to a ligand that binds specifically to the stalk of pIgR. In turn, this complex can be linked to defective adenovirus. Curiel and co-workers have demonstrated that naked plasmid DNA bound electrostatically to poly-L-lysine or poly-L-lysine-transferrin which has been linked to defective adenovirus mutants can be delivered to cells with transfection efficiencies approaching 90%. The adenovirus-poly-L-lysine-DNA conjugate binds to the normal adenovirus receptor and is subsequently internalized by receptor-mediated endocytosis. This approach has been used to obtain as much as a 1000-fold increase in expression of gene therapy vectors. Herpes viruses have similar properties. Curiel et al (1991) *Proc Natl Acad Sci USA* 88:8850–8854; Cotten et al (1992) *Proc Natl Acad Sci USA* 89:6094–6098; Curiel et al (1992) *Hum Gene Ther* 3:147–154; Wagner et al. (1992) *Proc Natl Aced Sci USA* 89:6099–6103; Michael et al. (1993) *J Biol Chem* 268:6866–6869; Curiel et al (1992) *Am J Respir Cell Mol Biol* 6:247–252, and Harris et al. (1993) *Am J Respir Cell Mol Biol* 9:441–447); Gao et al. (1993) *Hum. Gene Ther.* 4:17–24; Curiel et al U.S. patent application Ser. No. 07/768, 039.

In yet another approach using influenza virus, a hydrophobic peptide in the hemagglutinin can act as a fusion peptide at low pH to effect fusion of the virus with the membrane of the endosome and delivering the virus into the cytoplasm. This peptide has been used in transferrin/peptide/poly-L-lysine/DNA complexes for gene transfer using the transferrin receptor and substantially improved the efficiency of expression. Wagner et al., *Proc. Natl. Acad. Sci USA* 89:7934–7938 (1992). This peptide can be engineered into a ligand for transport of the ligand, or a portion thereof, out of the endosome.

A further approach may employ ricin A. Ricin A chain is capable of penetrating out of endosome and into the cytosol. Beaumell et al., J. Biol. Chem. 268:23661–23669 (1993). A ligand of the present invention may be linked to ricin A, such as by genetic fusion or chemical linkers.

Although the present invention has been described in some detail by way of illustration and example for purposes of clarity of understanding, it will be obvious that certain changes and modifications may be practiced within the scope of the appended claims.

EXAMPLE 1

Example 1 describes a method of producing and assaying for chicken antibodies and Fab fragments which specifically bind to the rabbit pIgR stalk region.

The membrane-spanning segment of the rabbit pIgR begins at the Valine residue at position 630. The sequence of the twenty four extracellular residues of the rabbit pIgR that precede the membrane-spanning segment is: 607-AspProAlaSerGlySerArgAlaSer-ValAspAlaSerSerAlaSerGlyGlnSerGlySerAlaL ys-629 (SEQ ID NO:7).

Two peptides were synthesized (Immuno-Dynamics, Inc., La Jolla, Calif.) representing the extracellular, membrane proximal 16 and 23 amino acids of pIgR. A C-terminal cysteine was added for conjugation purposes. Peptide sequences (in single letter code) were: DPA SGS RAS VDA SSA SGQ SGS AKC (SEQ ID NO:8) for the primary peptide; and the subsequence peptide: ASV DAS SAS GQS GSA KC (SEQ ID NO:9). Half of each amount of peptide was conjugated to keyhole limpet hemocyanin (KLH) (by Immuno-Dynamics, Inc).

The KLH-conjugated peptides were sent to Lampire Biological Laboratories (Pipersville, Pa.) for production of chicken antibodies in two chickens per peptide. Lampire's standard protocol for chicken immunization was followed by collection of pre-immune eggs and a pre-immune test bleed; intramuscular injection of 2 mg of peptide with Freund's complete suspension at project initiation; intramuscular injection of 0.5 mg of peptide with Freund's incomplete suspension week 1; intramuscular injection of 0.25 mg of peptide with Freund's incomplete suspension week 2; rest week 3; intramuscular injection of 0.25 mg of peptide with Freund's incomplete suspension week 4; rest week 5, and test bleed week 6. Daily egg collection began around week 6 and monthly test bleeds were collected. Eggs were delivered monthly.

Upon arrival, egg yolks were carefully separated from egg whites, and stored at 4° C. in 50–80 mls of basic buffer (0.01M sodium phosphate pH 7.5, 0.1M NaCI, 0.01% azide) per egg yolk until processed for extracting chicken antibody ("IgY"). IgY was extracted from batches of stored egg yolks by a series of PEG precipitations followed by a series of ammonium sulfate precipitations, according to the method of Poison et al. *Immunol Commun.* 9:475 (1980)). Briefly, solid PEG (polyethylene glycol, MW 8000) was added to yolks in basic buffer to 3.5% by weight of PEG to volume of diluted yolk, and stirred at room temperature until dissolved. The solution was centrifuged at 14,000 g for 10 min at 20° C. and decanted through a funnel containing a loose layer of absorbent cotton gauze. More PEG was added to the clear filtrate for a final PEG concentration of 12% to precipitate the IgY. After sedimenting the precipitate by centrifuging at 14,000 g for 10 min at 20° C., the precipitate was dissolved in 60 ml of basic buffer per yolk and an equal volume of 24% PEG in basic buffer was added to reform the precipitate. The precipitate was centrifuged twice more at 14,000 g for 10 min at 20° C. to remove all residual PEG solution. Pellets were dissolved in 30 mls of basic buffer per egg yolk, and the protein was precipitated in 50% saturated (NH4)2SO4 by slowly adding an equal volume of saturated (NH4)2SO4. and by stirring overnight at 4° C. The precipitate was centrifuged at 14,000 g for 10 min at 4° C. and the pellet was washed in an equal volume of cold 50% (NH4)2SO4. The precipitate was centrifuged again at 14,000 g for 10 min at 4° C., dissolved in PBS without calcium or magnesium, pH 7.5, and dialyzed extensively in PBS to remove all (NH4)2SO4. Purity of the IgY preparation was confirmed by SDS-PAGE (approx. 90–95%), and quantitation of IgY was estimated my measuring the absorbance at 280 nm and using an extinction coefficient of 1.3.

Affinity purification of IgY from chickens injected with the primary peptide of SEQ ID NO:8 was accomplished by first covalently linking the peptide to SULFOLINK coupling gel (Pierce Chemical Company), which allows binding specifically to sulfhydryl groups such as that on the C-terminal cysteine of the peptide. A 3 ml column was made with 3 mg of peptide according to the product instructions. Briefly, a 3 ml column was equilibrated with 6 column volumes of 50 mM Tris, 5 mM EDTA, pH 8.5, and then 3 mg of the primary peptide SEQ ID NO:8 in 3 ml 50 mM Tris, 5 mM EDTA pH 8.5 were added to the column for mixing at room temperature for 15 min. The column gel and peptide were incubated for another 30 min without mixing. The peptide buffer was drained off the gel and saved for later testing to confirm coupling efficiency using Ellman's reagent (DTNB (5,5'-dithiobis(2-nitrobenzoic acid), Pierce Chemical Company) which detects sulthydryl groups. The primary peptide SEQ ID NO:8 does not contain any aromatic amino acid groups and could not be detected spectrophotometrically or by standard protein assay techniques, such as by Bradford analysis. Using Eliman's reagent according to the product instructions for comparison of an aliquot of peptide solution before and after binding to the gel, confirmed 100% binding efficiency. The gel column was washed with 3 column volumes of 50 mM Tris, 5 mM EDTA pH 8.5 before blocking nonspecific binding sites with 3 ml of cysteine solution in 50 mM Tris, 5 mM EDTA pH 8.5 for 15 min mixing at room temperature followed by 30 minutes without mixing. The column was drained, and washed with 16 column volumes of 1M NaCl and then with 16 column volumes of degassed 0.05% sodium azide.

IgY was affinity purified on this peptide-linked SULFOLINK gel according to a modified version of Rosol et al. Veterinary Immunology and Immunopathology, 35:321–337, 1993. Once at room temperature, the column was washed with 10 column volumes of PBS. IgY was recycled on the column for 2 hours. The column was then washed with 10 column volumes of PBS followed by 10 column volumes of phosphate buffered saline (PBS) with 0.5M NaCl. Peptide-specific IgY was eluted with 500 mM glycine pH 2.5 and neutralized with 1M Tris pH 9.5. A UV spectrophotometer and graphing apparatus were used to follow the washing and elution of protein off the column. Samples with a signal at OD280 nm were concentrated in a centriprep 30 (Amicon) to a volume of 500–600 µl.

Fab fragments ("Yab fragments") were made from affinity purified IgY incubated with immobilized pepsin (Pierce Chemical Company) according to product instructions and modified from the method of Akita and Nakai. Journal of Immunological Methods. 162:155–164, 1993. Pepsin slurry was washed twice with 16 times the volume of 50 mM sodium acetate buffer pH 4.2, and resuspended in twice the volume of sodium acetate buffer. Affinity purified IgY was incubated with the immobilized pepsin at 37=BOC and mixed for 5 hour. One molar Tris-HCl pH 8.0 was added to give a final pH of 7.5. The pepsin mixture was centrifuged at 1000 g for 5 min and the supernatant containing the fragments was added to a CENTRICON 10 filter (Amicon) to remove small Fc fragments. Complete cleavage was confirmed by SDS-PAGE.

Chicken serum from successive test bleeds and IgY extracted from batches of pooled egg yolks were tested by ELISA to confirm recognition of the peptide. Affinity purified IgY and Fab' fragments ("Yab") were tested for their ability to recognize intact pIgR by western blot. Cell lysates were made from Madin-Darby canine kidney (MDCK) cells and MDCK cells transfected with rabbit pIgR ("pWe"), according to the method of Breitfeld et al. (Methods in Cell Biology 32:329–337 (1989)) using 10% NP40 lysis buffer containing 1 µg/ml of protease inhibitors and phenylmethylsulfonyl fluoride (PMSF). Cell lysates were run on a 10% gel under reducing conditions and transferred onto a PVDF (polyvinyidifluoride) membrane (Millipore, Bedford, MA). A mouse monoclonal antibody to the cytoplasmic portion of pIgR, SC166 (Solari et al., Cell, 36:61–71 (1984)), was used as a positive control antibody, and IgY isolated from pre-immune yolks was used as a negative control. HRP-conjugated rabbit anti-chicken IgY (Jackson Immunochemicals) and HRP-conjugated rabbit anti-mouse (Biorad) were used as secondary antibodies. IgY from a chicken injected with the primary peptide and IgY from a chicken injected with the subsequence peptide recognized intact pIgR, but IgY from one of the chickens injected with the subsequence antibody did not. Immunofluorescence studies of IgY and Yab fragments (from chickens injected with the primary peptide) with MDCK and pWe cells grown on coverslips, fixed with 4% paraformaldehyde and permeabilized with saponin showed more specific staining of the pIgR-transfected cells (FITC-conjugated rabbit anti-chicken and anti-mouse antibodies obtained from Jackson Immunochemicals). A cell ELISA (modified from M Hahne et al., Journal of Cell Biology. 121:655–64, 1993) on fixed and permeabilized cells showed Yab fragment staining 5-fold greater with pWe cells than MDCK cells. These data demonstrate that we have successfully raised polyclonal antibodies against the rabbit pIgR stalk peptide and that they recognize intact pIgR.

EXAMPLE 2

Example 2 describes selection of human recombinant single chain variable region fragment (scFv) antibodies by phage display.

Selection of scFv by phage display requires a soluble biotinylated antigen or antigen immobilized on a solid support. Because scFv selected by phage display tend to be low affinity binders and because the soluble antigen may allow selection of higher affinity scFv (R Schier et al., J. Mol. Biol. 255:28–43, 1996), the selection approach with soluble antigen was chosen. The pIgR stalk primary peptide, described in Example 1, corresponding to the 23 amino acids of the membrane-proximal extracellular part of the rabbit pIgR was conjugated to biotin via the sulfhydryl group of the cysteine residue using biotin-BMCC ((1-Biotinamido-4-(4' [maleimidomethyl] cyclohexane-carboxamido) butane) (Pierce Chemical Company, Rockford, Ill.) based on the method described in the product instructions. To ensure that the peptide had not dimerized via the sulfhydryl groups, the peptide was first reduced with 1% sodium borohydride in 0.1M Tris, 5 mM EDTA pH 8.0. The pH of the solution was lowered to pH 5 by adding 1 N HCl. Once the solution had finished fizzing, 1M Tris was added back to reach pH 7.0. A 8.5 mM biotin-BMCC solution was prepared by dissolving the biotinylation reagent in DMSO. A 5-fold molar excess of biotin-BMCC was added to the reduced peptide and incubated overnight at 4° C. The biotinylated peptide was separated from free biotin by HPLC with a C18 column with a gradient ranging from 10 to 50% CH3CN over 30 min, with UV detection at 215 nm. Mass spectrometry by electrospray and LSIMS (liquid secondary ion mass spectrometry) identified the correct peak corresponding to the biotinylated peptide.

The biotinylated primary peptide was incubated with a phage library encoding a large number of different human scFv (approx. $10^{10}$). This phage library was prepared as previously described (J D Marks et al., *J. Mol. Biol.* 222:581–97, 1991; J D Marks et al., *Bio/Technology* 10;779–783, 1992; J D Marks et al, *Bio/Technology* 11:1145–1149, 1993; A D Griffiths et al., *EMBO J* 12:725–734, 1993). A total of four rounds of selection, phagemid rescue and expansion in Escherichia coli suppressor strain TG-1 were performed as described in Marks et al. (*J. Mol. Biol.* 222:581–97, 1991) with the following modifications. The phage library used is known to contain several streptavidin binders, so the first three rounds of selection included a preclearing step with two 30 min incubations of the phage with streptavidin agarose (Sigma). The phage were then incubated with 5 μg of biotinylated primary peptide for 1 hour. To bind the biotinylated peptide with the attached phage, the peptide-phage solution was incubated with avidin magnetic beads on the first and third rounds for 15 and 5 minutes, respectively, and with streptavidin magnetic beads on the second and fourth rounds for 10 and 5 minutes, respectively. Rescued phage from the fourth round of selection were infected into *Escherichia coli* non-suppressor strain HB2151, and individual phagemid clones were induced to produce soluble scFv fragments with IPTG as described in Marks et al. (*J. Mol. Biol.* 222:581–97, ((1991)).

Bacterial supernatants from the individual clones were analysed for expression of soluble scFv fragments in a dot blot assay and for binding to biotinylated primary peptide in an ELISA assay (Finnern et al., *Clin. Exp. Immunol.* 102:566–574, 1995). The ELISA assay, however, was modified in the following manner: 96-well microwell plates (Immulon-4) were coated with avidin (10 μg/ml in phosphate buffered saline (PBS)) overnight at 4° C., washed 3 times with PBS, blocked with 2% milk in PBS and bound with biotinylated primary peptide (5 μg/ml in PBS). TMB (3,3',5,5' tetramethylbenzidine) solution (Kirkegaard and Perry) was used as substrate (100 μl/well), and the reaction was stopped with 0.1 8M H2SO4 before reading the color reaction in an ELISA reader at a wavelength of 450 nm. Dot blot analysis showed that 66% of the 96 selected colonies of HB2151 infected with phage rescued from the fourth round of selection produced scFv. ELISA assay showed that 43 of the 96 colonies produces scFv that bound to the peptide.

The diversity of all positive clones was determined by PCR screening. The scFv insert of the heavy and light chain was first amplified with the primers LMB3 and fd-Seq1 (Marks et al., *J. Mol. Biol.* 222:581–97, 1991), and then digested with the restriction enzyme BstNI. Clones with different DNA fingerprint patterns were sequenced using a SequiTherm Long-Read cycle sequencing kit (Epicentre Technologies) and a Licor machine. Five unique sequences were identified.

To obtain large amounts of purified scFv for further characterization and use, the five unique scFv were subcloned into the expression vector pUC119 Sfi-NotmycHis, which adds a hexa-histidine tag at the C-terminal end of the scFv (Schier et al., *J. Mol. Biol.*, 255:28–43, 1996).

EXAMPLE 3

Example 3 describes targeting of the wildtype cystic fibrosis transconductance regulator (CFTR) gene into mammalian cells expressing pIgR using a variation of the methods disclosed in Ferkol et al., *J. Clin. Invest.*, 92:2394–2400 (1993); and Ferkol et al., *J. Clin. Invest.*, 95:493–502 (1995), each of which is incorporated herein by reference.

An Fab fragment reactive to the stalk region of pIgR is made and purified by techniques such as that disclosed in Example 1. The Fab is linked to poly (L-lysine) (MW 20,000 Daltons) using the heterobifunctional crosslinking reagent N-succinimidyl 3-(2-pyridyidithio) propionate (SPDP) according to the method of Ferkol et al. (1993).

A plasmid comprising the CFTR gene is ligated to a cytomegalovirus early promoter and inserted into the vector pCB6. Thomas et al., *J. Biol Chem.*, 268:3313–3320 (1993). Complexes of Fab-polylysine-DNA are made by combining plasmid DNA with the Fab-polylysine in 3M NaCl.

The complex is introduced by dissolving it in 0.1 ml of phosphate buffered saline, and placing it into the nares of pathogen-free Sprague-Dawley rats (250–300 grams) lightly anesthetized with Metofane inhalant anesthesia. A micropipet will be used to apply 100 μL of the plasmid in PBS directly into the nares of rats that are manually restrained in the supine position. Rats will be held in this position until the solution has been inhaled. This technique has been shown to result in effective application of the sample onto the nasal mucosa. Shahin et al., Infection and Immunity 60:1482–1488 (1992); Gizurarson et al., Vaccine 10:101–106 (1992). Transcription of the transfected gene is assayed by immunofluorescence assay of production of the CFTR protein.

EXAMPLE 4

Example 4 describes a means of in vivo targeting of exogenous proteins into cells expressing pIgR.

An efficient method to allow egress of proteins from endosomes will employ the protein-Fab complex coupled to adenovirus. This method has been used with a number of receptor systems resulting in as much as a 1000-fold increase in expression. Curiel et al., *J. Respir. Cell Mol. Biol.* 6:247–252 (1992); Curiel et al., *Proc. Natl. Acad. Sci. USA* 88:8850–8854 (1991), Gao et al., *Hum. Gene Ther.* 4:17–24 (1993), each of which is incorporated herein by reference. Coupling is accomplished by biotinylation of the adenovirus and the Fab/poly-lysine followed by cross-linking with avidin. The resultant complex is administered as in Example 4.

EXAMPLE 5

Example 5 describes transcytosis of antibodies, which specifically bind to the stalk, from the apical to basolateral membrane of a MDCK (Madin Darby canine kidney) cell comprising pIgR.

Yab fragments reactive to pIgR were made as described in Example 1. Anti-pIgR stalk Yab fragments were radio-iodinated by the iodine monochloride method of Goldsein et al. (*Meth. Enzymol.* 96:241–249, 1983). Radio-iodinated IgA was used as a control ligand. Radio-iodinated Yab fragments or IgA ($10^7$ cpm in 100 μl/well) were added to the apical surface of MDCK and pWe cells grown in a polarized manner for 4 days on 12 mm diameter, 0.4 μm pore size cell culture inserts (Transwells, Costar). Breitfeld et al., *Methods in Cell Biology* 32:329–337 (1989). Radio-labelled Yab fragments were added to cells with and without a 2 h preincubation with the protease inhibitor, leupeptin, 50 μl/ml. After 20 min of apical uptake at 37° C., unbound radio-labelled ligand was washed with MEM (minimal essential medium)/BSA (bovine serum albumen) three times quickly, one 5 min wash and two more quick washes. The apical and basolateral media were collected and changed at 7, 15, 30, 60 and 120 min time points for quantitation in a gamma counter (Beckman Instruments, Palo Alto, Calif.). Cell culture inserts were cut out at 120 min for quantitation in a gamma counter and to calculate the total initial uptake of radioactivity. The background uptake by MDCK cells was subtracted from that by pWe cells to calculate specific recycling and transcytosis of the radiolabeled ligands. The results showed that 13–18% of the Yab fragments were transcytosed from the apical to the basolateral surface of cells pretreated with leupeptin, in contrast to 5–6% of the IgA.

All publications and patents mentioned in this specification are herein incorporated by reference into the specification to the same extent as if each individual publication or patent was specifically and individually indicated to be incorporated herein by reference.

What is claimed is:

1. An antibody that binds specifically to the stalk of a polymeric immunoglobulin receptor (pIgR) of a cell with the proviso that the antibody does not substantially bind to secretory component of pIgR under physiological conditions.

2. An antibody of claim 1 wherein the antibody is an Fab.

3. An antibody of claim 1 wherein the antibody is a humanized antibody.

4. An antibody of claim 1 wherein the antibody is a recombinant single chain variable region fragment of an antibody.

5. An antibody of claim 1 which binds to a peptide selected from the group consisting of:

Mouse: Glu-Arg-Glu-Ile-Gln-Asn-Val-Arg-Asp-Gln-Ala-Gln-Glu-Asn-Arg-Ala-Ser-Gly-Asp-Ala-Gly-Ser-Ala-Asp-Gly-Gln-Ser-Arg-Ser-Ser-Ser-Ser-Lys (SEQ ID NO:2)

Rat: Glu-Arg-Glu-Ile-Gln-Asn-Ala-Gly-Asp-Gln-Ala-Gin-Glu-Asn-Arg-Ala-Ser-Gly-Asn-Ala-Gly-Ser-Ala-Gly-Gly-Gln-Ser-Gly-Ser-Ser-Lys (SEQ ID NO:3)

Human: Glu-Lys-Ala-Val-Ala-Asp-Thr-Arg-Asp-Gln-Ala-Asp-Gly-Ser-Arg-Ala-Ser-Val-Asp-Ser-Gly-Ser-Ser-Glu-Glu-Gln-Gly-Gly-Ser-Ser-Arg (SEQ ID NO:4)

Bovine: Glu-Ser-Val-Lys-Asp-Ala-Ala-Gly-Gly-Pro-Gly-Ala-Pro-Ala-Asp-Pro-Gly-Arg-Pro-Thr-Gly-Tyr-Ser-Gly-Ser-Ser-Lys (SEQ ID NO: 5) and Rabbit: Leu-Ala-Glu-Val-Ala-Val-Gln-Ser-Ala-Glu-Asp-Pro-Ala-Ser-Gly-Asp-Pro-Ala-Ser-Gly-Ser-Arg-Ala-Ser-Val-Asp-Ser-Gly-Ser-Ser-Glu-Glu-Gln-Gly-Gly-Ser-Ser-Arg-Ser-Lys (SEQ ID NO: 6).

6. An antibody of claim 1 which is further defined as having a binding component for selectively binding to the receptor stalk and a biologically active component wherein the biologically active component is selected from the group consisting of a nucleic acid, protein, radioisotope, lipids, and carbohydrates.

7. An antibody of claim 6 wherein the nucleic acid encodes the wildtype cystic fibrosis transmembrane conductance regulator.

8. An antibody of claim 1 which is further defined as having a binding component for selectively binding to the receptor stalk and a biologically active component wherein the biologically active component is selected from the group consisting of anti-inflammatories, antisense oligos, antibiotics, and anti-infectives.

9. The antibody of claim 1 wherein the antibody specifically binds only to the stalk.

* * * * *

SEQUENCE LISTING (1) GENERAL INFORMATION:

(iii) NUMBER OF SEQUENCES: 11

(2) INFORMATION FOR SEQ ID NO: 1:

(i) SEQUENCE CHARACTERISTICS:
      (A) LENGTH: 4 amino acids
      (B) TYPE: amino acid
      (C) STRANDEDNESS: <Unknown>
      (D) TOPOLOGY: linear (ii) MOLECULE TYPE: peptide (ix) FEATURE:
      (A) NAME/KEY: Modified-site
      (B) LOCATION: 3
      (D) OTHER INFORMATION: /product= "OTHER" /note= "Xaa = polar
          or charged amino acid"

(xi) SEQUENCE DESCRIPTION: SEQ ID NO: 1:

Phe Ala Xaa Glu
1

(2) INFORMATION FOR SEQ ID NO: 2:

(i) SEQUENCE CHARACTERISTICS:
      (A) LENGTH: 33 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 2:

Glu Arg Glu Ile Gln Asn Val Arg Asp Gln Ala Gln Glu Asn Arg Ala
1               5                   10                  15

Ser Gly Asp Ala Gly Ser Ala Asp Gly Gln Ser Arg Ser Ser Ser Ser
            20                  25                  30

Lys (2) INFORMATION FOR SEQ ID NO: 3:

(i) SEQUENCE CHARACTERISTICS:
      (A) LENGTH: 31 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 3:

Glu Arg Glu Ile Gln Asn Ala Gly Asp Gln Ala Gln Glu Asn Arg Ala

```
1               5                    10                   15
Ser Gly Asn Ala Gly Ser Ala Gly Gly Gln Ser Gly Ser Ser Lys
            20                  25                  30
```

(2) INFORMATION FOR SEQ ID NO: 4:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 4:

```
Glu Lys Ala Val Ala Asp Thr Arg Asp Gln Ala Asp Gly Ser Arg Ala
1               5                   10                  15
Ser Val Asp Ser Gly Ser Ser Glu Glu Gln Gly Gly Ser Ser Arg
            20                  25                  30
```

(2) INFORMATION FOR SEQ ID NO: 5:

(i) SEQUENCE CHARACTERISTICS:
        (A) LENGTH: 27 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 5:

```
Glu Ser Val Lys Asp Ala Ala Gly Gly Pro Gly Ala Pro Ala Asp Pro
1               5                   10                  15
Gly Arg Pro Thr Gly Tyr Ser Gly Ser Ser Lys
            20                  25
```

(2) INFORMATION FOR SEQ ID NO: 6:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

```
Leu Ala Glu Val Ala Val Gln Ser Ala Glu Asp Pro Ala Ser Gly Asp
1               5                   10                  15
Pro Ala Ser Gly Ser Arg Ala Ser Val Asp Gly Ser Ser Glu Glu
            20                  25                  30
Gln Gly Gly Ser Ser Arg Ser Lys
        35                  40
```

(2) INFORMATION FOR SEQ ID NO: 7:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Asp Pro Ala Ser Gly Ser Arg Ala Ser Val Asp Ala Ser Ser Ala Ser

```
1               5                   10                  15
Gly Gln Ser Gly Ser Ala Lys
            20
```

(2) INFORMATION FOR SEQ ID NO: 8:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

```
Asp Pro Ala Ser Gly Ser Arg Ala Ser Val Asp Ala Ser Ser Ala Ser
1               5                   10                  15
Gly Gln Ser Gly Ser Ala Lys Cys
            20
```

(2) INFORMATION FOR SEQ ID NO: 9:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

```
Ala Ser Val Asp Ala Ser Ser Ala Ser Gly Gln Ser Gly Ser Ala Lys
1               5                   10                  15
Cys
```

(2) INFORMATION FOR SEQ ID NO: 10:

(i) SEQUENCE CHARACTERISTICS:
        (A) LENGTH: 61 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 10:

```
Ala Asp Ala Ala Pro Asp Glu Lys Val Leu Asp Ser Gly Phe Arg Glu
1               5                   10                  15
Ile Glu Asn Lys Ala Ile Gln Asp Pro Arg Leu Phe Ala Glu Glu Lys
            20                  25                  30
Ala Val Ala Asp Thr Arg Asp Gln Ala Asp Gly Ser Arg Ala Ser Val
        35                  40                      45
Asp Ser Gly Ser Ser Glu Glu Gln Gly Gly Ser Ser Arg
    50                  55                  60
```

(2) INFORMATION FOR SEQ ID NO: 11:

(i) SEQUENCE CHARACTERISTICS:
        (A) LENGTH: 61 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 11:

-continued

```
Ala Asp Ala Ala Pro Asp Glu Lys Val Leu Asp Ser Gly Phe Arg Glu
1               5                   10                  15

Ile Glu Asn Lys Ala Ile Gln Asp Pro Arg Leu Phe Ala Glu Glu Lys
            20                  25                  30

Ala Val Ala Asp Thr Arg Asp Gln Ala Asp Gly Ser Arg Ala Ser Val
        35                  40                  45

Asp Ser Gly Ser Ser Glu Glu Gln Gly Gly Ser Ser Arg
    50                  55                  60
```